United States Patent [19]

Laurent et al.

[11] Patent Number: 4,681,875

[45] Date of Patent: Jul. 21, 1987

[54] 3,17 β-ESTRIOL DIESTERS, METHODS OF THEIR USE, AND PHARMACEUTICAL PREPARATIONS CONTAINING THEM

[75] Inventors: Henry Laurent; Dieter Bittler; Sybille Beier; Walter Elger, all of Berlin, Fed. Rep. of Germany

[73] Assignee: Schering Aktiengesellschaft, Berlin and Bergkamen, Fed. Rep. of Germany

[21] Appl. No.: 734,737

[22] Filed: May 16, 1985

[30] Foreign Application Priority Data

May 16, 1984 [DE] Fed. Rep. of Germany ....... 3418562

[51] Int. Cl.[4] .................... C07J 00/00; A61K 31/56
[52] U.S. Cl. .................................. 514/182; 260/397.5
[58] Field of Search ..................... 260/397.5; 514/182

[56] References Cited

PUBLICATIONS

Chem. Abstracts (1970) vol. 72, No. 23 Par. 121768b, an abstract of a publication by Beslin et al., "Bull. Soc. Chim. Fir." 1970 (3) pp. 959–965.

Primary Examiner—Leonard Schenkman
Assistant Examiner—Joseph A. Lipovsky
Attorney, Agent, or Firm—Millen & White

[57] ABSTRACT

Estriol esters of Formula I

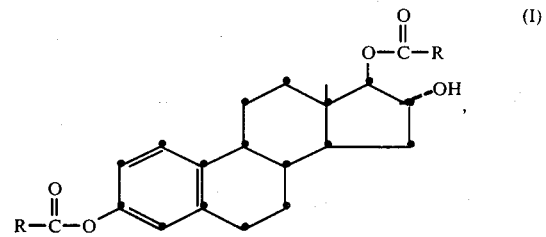

wherein
R, in each case, means the residue of a monocarboxylic acid of 2–10 carbon atoms.

The novel estriol esters surpass estriol in strength and duration of estrogen effect.

19 Claims, No Drawings

3,17 β-ESTRIOL DIESTERS, METHODS OF THEIR USE, AND PHARMACEUTICAL PREPARATIONS CONTAINING THEM

BACKGROUND OF THE INVENTION

The invention relates to 3,17β-estriol diesters according to the claims, processes for their production, and pharmaceutical preparations containing the novel estriol esters.

SUMMARY OF THE INVENTION

It is an object of the invention to provide compounds having valuable pharamcological properties, processes for their production and methods for their use.

Upon further study of the specification and appended claims, further objects and advantages of this invention will become apparent to those skilled in the art.

These objects have been achieved by providing estriol esters of Formula I

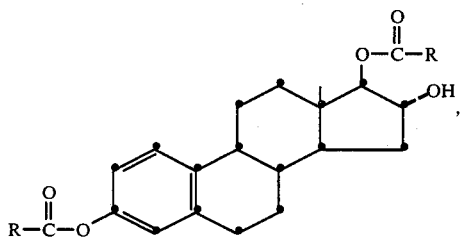

wherein
RCOO, in each case, is the residue of a monocarboxylic acid of 2-10 carbon atoms.

DETAILED DISCUSSION OF THE INVENTION

Estriol, having the chemical name of 1,3,5(10)-estratriene-3,16α,17β-triol, is an important natural estrogen.

Estriol is also utilized as the active ingredient in preparations for estrogen substitution in cases of estrogen deficiency, for example in postmenopausal women.

Since estriol is eliminated from the body very rapidly, it must be administered in short intervals (one to three times daily).

Several esters of estriol have also been described in the literature, for example estriol triesters, 16,17-diesters and 16-monoesters in Chem. Pharm. Bull. 11: 510–514 (1963), furthermore 3-acetate, 3,16-diacetate and 16,17-diacetate in Acta Cehm. Scand. 22: 254 (1968).

With the exception of estriol succinate, which must be administered three times daily, no estriol esters have been utilized as medicines.

The 3,17β-diesters of estriol with monocarboxylic acids of 2-10 carbon atoms, not disclosed heretofore, surpass estriol in potency and duration of estrogen effect.

The ester residues in Formula I can be derived from an aliphatic, cycloaliphatic-aliphatic or aromatic monocarboxylic acid. In each case, these are preferably hydrocarbon in nature. The cyclic moiety generally has 3-7 C-atoms. Preferred ester residues R are those of acetic acid, propionic acid, butyric acid, isobutyric acid, pivalic acid, valeric acid, caproic acid, enanthic acid, octanoic and decanoic acid, furthermore β-cyclopentylpropionic acid and benzoic acid.

A metabolically stabilized form of a natural estrogen is obtained by esterifying estriol in the 3,17-position. These esters have variegated uses in medicine. Primary areas of usage of the novel estriol esters are substitution of estrogens in postmenopausal women suffering from climacteric deficiency symptoms such as hot flashes, osteoporosis, atrophy of skin and genitals; furthermore fertility control in women; and gynecological indications, such as, for example, vaginal atrophy, kraurosis vulvae, etc.

The pharmacologically active compounds of this invention can be processed in accordance with conventional methods of galenic pharmacy to produce medicaments for administration to patients, e.g., mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to those wherein the active ingredients can be dissolved or suspended, i.e., water (with or without the addition of electrolyte salts or thickeners) salt solutions, alcohols, gum arabic, oils, e.g., vegetable oils (with or without the addition of a solubilizer, a surfactant, a suspension or emulsifying agent), polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethycellulose, polyvinyl pyrrolidone, etc. Examples for oils utilized are, in particular, olive oil, peanut oil, cottonseed oil, soybean oil, caster oil and sesame oil. Examples for solubilizers are especially benzyl alcohol and benzyl benzoate. A preferred mixture consists of 6 parts by weight of castor oil and 4 parts by weight of benzyl benzoate. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oil or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation; multiple coatings, etc. The parenteral method of administration is preferred because only in such a case will the advantages of the novel esters become fully apparent. By parenteral administration, initial liver passage and thereby rapid metabolizing are avoided. Furthermore, damaging hepatic estrogen effects are avoided by parenteral administration, such as, for example, rise in clotting factors, increase in hormone-transporting proteins, increase in angiotensinogens, and shift in equilibrium of lipoproteins.

The dosage administered can vary over a wide range and includes any effective amount. Generally, the compounds of this invention are dispensed in unit dosage form comprising 10-300 mg depending on the condition to be treated and the type and frequency of administration.

The dosage of the compounds according to this invention generally is 10–300 mg in 1 ml oil for 2, 3 or 4 weeks when administered to patients, e.g., humans, as a gynecologically active agent analogously to the known agent Progynon(R) Depot.

Dosages for a given host can be determined using conventional considerations, e.g., by customary comparison of the differential activities of the subject compound and of a known agent, e.g., by means of an appropriate, conventional pharmacological protocol.

The novel esters are especially suitable as a pro-drug of estriol for the preparation of injectable or implantable depot preparations. They also exhibit the advantage over orally administrable preparations that a single injection suffices for one or several months whereas, for example, tablets must be taken daily. Duration of the depot effect depends on the chain length and amount of the ester as well as on the type of carrier substance that releases the active agent, e.g., an aqueous microcrystalline suspension is suitable.

Implantation preparations can contain the active agent with inert materials, e.g., biodegradable polymers. The active ingredients can also be processed with silicone rubber into implants.

When using the novel estriol esters as depot contraceptives, the novel esters can be combined with a depot gestagen or a gestagen to be administered orally. The combined usage can be simultaneous, or staggered in time. Thus, a depot estrogen of Formula I and a depot gestagen can be combined, for example, into a one-month injection. Suitable as the depot gestagen of an oily solution is, for example, norethisterone enanthate and for a microcrystalline suspension, medroxyprogesterone acetate.

Depending on the desired duration of activity, about 10 to 300 mg of the novel depot estrogen can be combined with 30–300 mg of a depot gestagen.

It is also possible to inject the depot estrogen of this invention and to administer daily orally a customary gestagen, such as norethisterone, norgestrel, levonorgestrel or cyproterone acetate.

The novel compounds of Formula I are produced by esterification of an estriol-16-silyl ether of Formula II.

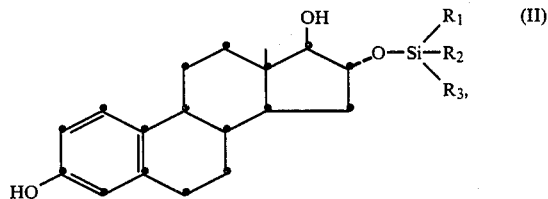

wherein $R_1$, $R_2$, $R_3$, being identical or different, mean respectively alkyl of 1–5 carbon atoms, phenyl or benzyl, and subsequently cleaving the silyl ether.

Esterification of the hydroxy groups in the 3- and 17$\beta$-positions of estriol-16-silyl ether takes place conventionally with the corresponding monocarboxylic acid RCOOH or a derivative, especially the anhydride or chloride of the monocarboxylic acid, in the presence of a base. Especially suitable as bases are tertiary amines, such as pyridine, 4-dimethylaminopyridine, collidine, triethylamine, or mixtures of these amines.

The subsequent cleavage of the silyl ether is also conducted according to conventional methods. A preferred method is cleavage with tetrabutylammonium fluoride in anhydrous tetrahydrofuran at room temperature.

The estriol-16-silyl ethers of Formula II utilized as the starting compounds are obtained by reacting estriol with the corresponding silyl chloride in the presence of imidazole in dimethylformamide. Examples for silyl chlorides are tert-butyldimethylsilyl chloride, dimethyl-2-(3-methylbutyl)silyl chloride, trimethyl-, triphenyl- and tribenzylsilyl chloride.

The estrogenic activity and depot properties of the novel estriol esters were determined in comparison with estriol ($E_3$) in a modified uterus growth test according to Rubin on ovariectomized rats (Endocrinology 49:429–439 (1951)].

Adult ovariectomized rats weighing about 150 g, 6 animals per dosage group, are treated once with the respective test or reference compound (estriol). The day of administering the compound is considered day 1 ($d_1$) of the experiment. The compounds are dissolved in a mixture of benzyl benzoate+castor oil in a ratio of 4:6, and the daily dose is administered subcutaneously (s.c.) in a volume of 0.2 ml. A control group receives only 0.2 ml of vehicle.

Active estrogens lead, in ovariectomized rats, to characteristic changes in the vaginal epithelium. Strong proliferation of vaginal epithelium occurs, and the superficial cell layers are cornified. Vaginal smears are taken once daily. The pictures of the smears are evaluated cytologically.

Differentiation is made among the following cycle stages:

1 = diestrus (leukocytes and nucleated epithelium cells)
2 = proestrus (nucleated epithelium cells)
3 = estrus (anucleated cornified plaques )
4 = metestrus (anucleated cornified plaques, leukocytes, epithelium cells)

For determining the duration of estrogen effect on the vagina, the period is recorded, in days on which estrus is maintained.

Table 1 shows that the animals remain in estrus for one day after administration of estriol ($E_3$); estrus is maintained for 8, 16, 23, 28 and 27 days, respectively, after administration of equimolar amounts of $E_3$ dipropionate, $E_3$ dibutyrate, $E_3$ diisobutyrate, $E_3$ divalerate and $E_3$ dihexanoate.

TABLE 1

Duration of Estrogen Effect on Vagina after One-Time Injection (s.c.) of Estriol ($E_3$) and Respectively One-Time Injection of Various 3,17-Diesters in Ovariectomized Rats in Equimolar Dosages

| Compound | Estrus |
|---|---|
| Estriol ($E_3$), 100 μg s.c. | 1 Day |
| $E_3$ Dipropionate, 139 μg s.c. | 8 Days |
| $E_3$ Dibutyrate, 149 μg s.c. | 16 Days |
| $E_3$ Diisobutyrate, 149 μg s.c. | 23 Days |
| $E_3$ Divalerate, 158 μg s.c. | 28 Days |
| $E_3$ Dihexanoate, 168 μg s.c. | 27 Days |

Table 2 indicates the chronological course of estriol ($E_3$) serum concentration in pmol/l after a one-time injection (s.c.) of estriol ($E_3$) and respectively one-time injection (s.c.) of various $E_3$ 3,17-diesters in ovariectomized rats.

Blood is drawn from the animals on the first day, 2 hours prior to injection; on the 5th, 10th, 15th, 20th, 25th and 30th day after injection in order to determine the serum $E_3$ concentration by means of RIA (radioimmunoassay).

Table 2 reveals that, after administration of estriol 3,17-diesters, the $E_3$ concentration as measured by radioimmunology is 5–15 times higher than after equimolar administration of estriol ($E_3$).

In case of the diesters, increased $E_3$ concentrations are observed for up to 30 days after administration, in case of estriol merely for 8 days.

TABLE 2

Chronological Course of $E_3$ Serum Concentration [pmol/l] after One Time Injection (s.c.) of Estriol ($E_3$) and Respectively One-Time Injection (s.c.) of Various 3,17-Diesters in Ovariectomized Rats in Equimolar Doses

| Compound | Day 1* | Day 5 | Day 10 | Day 15 | Day 20 | Day 25 | Day 30 |
|---|---|---|---|---|---|---|---|
| Estriol ($E_3$), 100 μg s.c. | 37.2 | 63.6 | Day 8: 57.0 | | | | |
| $E_3$ Dipropionate, 139 μg s.c. | 49.2 | 1047.9 | 159.2 | 106.8 | | | |
| $E_3$ Dibutyrate, 149 μg s.c. | 41.0 | 990.5 | 251.5 | 124.0 | 62.5 | Day 24: 46.7 | |
| $E_3$ Diisobutyrate, 149 μg s.c. | 34.0 | 691.7 | 280.7 | 213.2 | 96.5 | 77.8 | 50.7 |
| $E_3$ Divalerate, 158 μg s.c. | 39.7 | 600.8 | 264.2 | 209.3 | 150.2 | 85.7 | 75.8 |
| $E_3$ Dihexanoate, 168 μg s.c. | 46.5 | 335.9 | 367.8 | 259.8 | 206.5 | 199.1 | 89.2 |
| $E_3$ Didecanoate, 207 μg s.c. | 55.7 | 179.0 | 188.8 | 170.6 | 155.0 | 109.0 | 92.9 |
| Solvent Control, s.c. | 39.9 | 39.8 | 39.3 | 37.1 | 36.7 | 36.0 | 50.3 |

*2 Hours prior to injection

It can be seen from the results of the animal experiments that potency of activity as well as duration of efficacy are increased by the esterification of estriol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation of the Starting Compound
16α-(tert-Butyldimethylsilyloxy)-1,3,5(10)-estratriene-3,17β-diol A solution of 11.52 g of 1,3,5(10)-estratriene-3,16α,17β-triol in 200 ml of dimethylformamide, cooled to −20° C., is combined, after adding 6.52 g of imidazole, dropwise with a solution of 13.24 g of tertbutyldimethylsilyl chloride in 100 ml of dimethylformamide. This reaction mixture is stirred for one hour with continued cooling and then poured into ice water. The resultant precipitate is filtered off, washed with water and dissolved in dichloromethane. The solution is dried over sodium sulfate and evaporated under vacuum. The residue is chromatographed on silica gel.

Yield: 11.30 g of 16α-(tert-butyldimethylsilyloxy)-1,3,5(10)-estratriene-3,17β-diol.

Melting point: 194° C.

EXAMPLES

Example 1

(a) A solution of 750 mg of 16α-(tert-butyldimethylsilyloxy)-1,3,5(10)-estratriene-3,17β-diol in 3 ml of pyridine is combined with 1.5 ml of acetic anhydride. After a reaction period of 20 hours at 20° C., the solution is poured into ice water. The thus-obtained precipitate is filtered off, washed with water, and dried, yielding 950 mg of 3,17β-diacetoxy-16α-(tert-butyldimethylsilyloxy)-1,3,5(10)-estratriene.

(b) 950 mg of 3,17β-diacetoxy-16α-(tert-butyldimethylsilyloxy)-1,3,5(10)-estratriene is dissolved in 9.5 ml of anhydrous tetrahydrofuran. The solution is combined with 950 mg of tetrabutylammonium fluoride and stirred for 2.5 hours at 20° C. The reaction mixture is combined with diethyl ether, washed with water, dried over sodium sulfate and evaporated under vacuum. The residue is chromatographed on silica gel with a pentane-diethyl ether gradient (0–20% diethyl ether).

Yield: 310 mg of 3,17β-diacetoxy-1,3,5(10)-estratriene-16α-ol, mp 132° C. (from diisopropyl ether). $[\alpha]_D = +96°$ (in chloroform).

Example 2

(a) A solution of 500 mg of 16α-(tert-butyldimethylsilyloxy)-1,3,5(10)-estratriene-3,17β-diol in 2 ml of pyridine is combined with 1.0 ml of propionic anhydride and allowed to stand for 48 hours at room temperature. The reaction solution is diluted with diethyl ether, washed with water, dried over sodium sulfate and evaporated under vacuum. The residue is chromatographed with a pentanediethyl ether gradient (0–20% diethyl ether).

Yield: 660 mg of 16α-(tert-butyldimethylsilyloxy)-3,17β-dipropionyloxy-1,3,5(10)-estratriene.

(b) 660 mg of 16α-(tert-butyldimethylsilyloxy)-3,17β-dipropionyloxy-1,3,5(10)-estratriene is reacted as described in Example 1(b) with tetrabutylammonium fluoride. After performing a corresponding working-up step, 220 mg of 3,17β-dipropionyloxy-1,3,5(10)-estratrien-16α-ol is obtained, mp 105° C. (from diisopropyl ether).

$[\alpha]_D^{22} = +90°$ (in chloroform).

Example 3

(a) A solution of 1.0 g of 16α-(tert-butyldimethylsilyloxy)-1,3,5(10)-estratriene-3,17β-diol in 4 ml of pyridine and 2 ml of butyric anhydride is allowed to stand, with the addition of 100 mg of 4-dimethylaminopyridine, for 20 hours at room temperature. Working up takes place as in Example 2(a). Yield: 1.4 g of 16α-(tert-butyldimethylsilyl.

(b) 1.4 g of 16α-(tert-butyldimethylsilyloxy)-3,17β-dibutyryloxy-1,3,5(10)-estratriene is reacted as described in Example 1(b). After a corresponding working-up step, 900 mg of 3,17β-dibutyryloxy-1,3,5(10)-estratrien-16α-ol is obtained as an oil.

$[\alpha]_D^{22} = +84°$ (in chloroform).

Example 4

(a) 1.0 g of 16α-(tert-butyldimethylsilyloxy)-1,3,5(10)-estratriene-3,17β-diol is reacted with isobutyric anhydride under the reaction conditions set forth in Example 3(a), thus obtaining 1.3 g of 16α-(tert-butyldimethylsilyloxy)-3,17β-diisobutyryloxy-1,3,5(10)-estratriene.

(b) 1.3 g of 16α-(tert-butyldimethylsilyloxy)-3,17β-diisobutyryloxy-1,3,5(10)-estratriene yields, under the conditions described in Example 1(b), 830 mg of 3,17β-diisobutyryloxy-1,3,5(10)-estratrien-16α-ol, mp 114° C.

$[\alpha]_D^{22} = +86°$ (in chloroform).

Example 5

(a) 1.0 g of 16α-(tert-butyldimethylsilyloxy)-1,3,5(10)-estratriene-3,17β-diol yields, with valeric anhydride under the conditions set forth in Example 3(a), 1.37 g of 16α-(tert-butyldimethylsilyloxy)-3,17β-divaleryloxy-1,3,5(10)-estratriene.

(b) Under the conditions described in Example 1(b), 1.37 g of 16α-(tert-butyldimethylsilyloxy)-3,17β-divaleryloxy-1,3,5(10)-estratriene yields 760 mg of 3,17β-divaleryloxy-1,3,5(10)-estratrien-16α-ol as an oil.

$[\alpha]_D^{22} = +79°$ (in chloroform).

Example 6

(a) From 750 mg of 16α-(tert-butyldimethylsilyloxy)-1,3,5(10)-estratriene-3,17β-diol, using caproic anhydride, 1.08 g of 16α-(tert-butyldimethylsilyloxy)-3,17β-dihexanoyloxy-1,3,5(10)-estratriene is obtained under the reaction conditions described in Example 3(a).

(b) Under the conditions described in Example 1(b), 1.08 g of 16α-(tert-butyldimethylsilyloxy)-3,17β-dihexanoyloxy-1,3,5(10)-estratriene yields 580 mg of 3,17β-dihexanoyloxy-1,3,5(10)-estratrien-16α-ol as an oil.

$[\alpha]_D^{22} = +75°$ (in chloroform).

Example 7

(a) With pivaloyl chloride, under the conditions disclosed in Example 3(a), 1.0 g of 16α-(tert-butyldimethylsilyloxy)-1,3,5(10)-estriene-3,17β-diol yields 1.38 g of 16α-(tert-butyldimethylsilyloxy)-3,17β-dipivaloyloxy-1,3,5(10)-estratriene.

(b) 1.38 g of 16α-(tert-butyldimethylsilyloxy)-3,17β-dipivaloyloxy-1,3,5(10)-estratriene is converted, under the conditions indicated in Example 1(b), into 1.10 g of 3,17β-dipivaloyloxy-1,3,5(10)-estratrien-16α-ol, mp 164° C.

$[\alpha]_D^{22} = +83°$ (in chloroform).

Example 8

(a) With decanoyl chloride, under the conditions described in Example 3(a), 750 mg of 16α-(tert-butyldimethylsilyloxy)-1,3,5(10)-estratriene-3,17β-diol yields 1.10 g of 16α-(tert-butyldimethylsilyloxy)-3,17β-didecanoyloxy-1,3,5(10)-estratriene.

(b) Under the conditions indicated in Example 1(b), 1.10 g of 16α-(tert-butyldimethylsilyloxy)-3,17β-didecanoyloxy-1,3,5(10)-estratriene is converted into 580 mg of 3,17β-didecanoyloxy-1,3,5(10)-estratrien-16α-ol, mp 64° C.

$[\alpha]_D^{22} = +63°$ (in chloroform).

Example 9

(a) Under the conditions set forth in Example 3(a), 1.0 g of 16α-(tert-butyldimethylsilyloxy)-1,3,5(10)-estratriene-3,17β-diol yields, with benzoyl chloride, 1.34 g of 3,17β-dibenzoyloxy-16α-(tert-butyldimethylsilyloxy)-1,3,5(10)-estratriene.

(b) Under the conditions set forth in Example 1(b), 1.34 g of 3,17β-dibenzoyloxy-16α-(tert-butyldimethylsilyloxy)-1,3,5(10)-estratriene is converted into 765 mg of 3,17β-dibenzoyloxy-1,3,5(10)-estratrien-16α-ol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An estriol ester of the formula

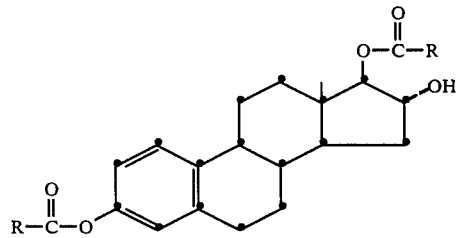

wherein

R, in each case, is a hydrocarbon aliphatic, cycloaliphatic-aliphatic or aromatic group of 3–10 carbon atoms.

2. A compound according to claim 1 which is 3,17β-Diisobutyryloxy-1,3,5(10)-estratrien-16α-ol.

3. A compound according to claim 1 which is 3,17β-Divaleryloxy-1,3,5(10)-estratrien-16α-ol.

4. A compound according to claim 1 which is 3,17β-Dihexanoyloxy-1,3,5(10)-estratrien-16α-ol.

5. A compound according to claim 1 which is 3,17β-Dipivaloyloxy-1,3,5(10)-estratrien-16α-ol.

6. A compound according to claim 1 which is 3,17β-Didecanoyloxy-1,3,5(10)-estratrien-16α-ol.

7. A compound according to claim 1 which is 3,17β-Dibenzoyloxy-1,3,5(10)-estratrien-16α-ol.

8. A compound according to claim 1 which is 3,17β-Dibutyryloxy-1,3,5(10)-estratrien-16α-ol.

9. A compound according to claim 1, wherein R is alkyl or phenyl.

10. A pharmaceutical composition comprising a 3,17β-estriol diester of claim 1 and a pharmaceutically acceptable carrier.

11. A composition of claim 10 which is a depot contraceptive.

12. A composition of claim 10, wherein the amount of the diester is 10–300 mg.

13. A composition of claim 10, further comprising a gestagenically effective compound.

14. A compound according to claim 1, which is 3,17β-Dienanthoyl-1,3,5(10)-estratrien-16α-ol.

15. A compound according to claim 1, which is 3,17β-Dioctanoyl-1,3,5(10)-estratrien-16α-ol.

16. A compound according to claim 1, which is 3,17β-Di-β-cyclopentylpropionyl-1,3,5(10)-estratien-16α-ol.

17. A compound according to claim 1, in isolated form.

18. A method of achieving a gynecological effect in a patient comprising administering an effective amount of a 3,17β-estriol diester of the formula:

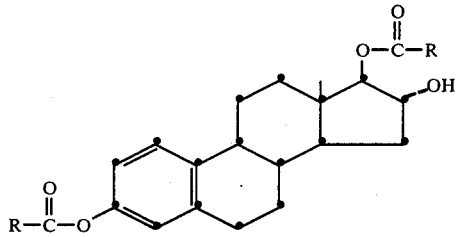

wherein
R, in each case, is a hydrocarbon aliphatic cycloaliphatic-aliphatic or aromatic group of 1-10 carbon atoms.

19. A method of treating climacteric deficiencies in a patient comprising administering an effective amount of a 3,17β-estriol diester of the formula:

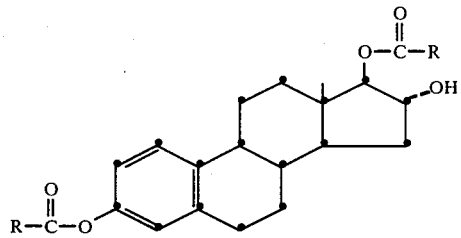

wherein
R, in each case, is a hydrocarbon aliphatic cycloaliphatic-aliphatic or aromatic group of 1-10 carbon atoms.

* * * * *